United States Patent
Choudhary et al.

(10) Patent No.: US 6,459,000 B1
(45) Date of Patent: Oct. 1, 2002

(54) PROCESS FOR THE LIQUID PHASE ACYLATION OF AROMATIC COMPOUNDS

(75) Inventors: Vasant Ramchandra Choudhary; Suman Kumar Jana, both of Maharashtra (IN)

(73) Assignee: Council of Scientific and Industrial Research, Pune (IN)

( * ) Notice: Subject to any disclaimer, the term of this patent is extended or adjusted under 35 U.S.C. 154(b) by 0 days.

(21) Appl. No.: 09/817,747

(22) Filed: Mar. 26, 2001

(51) Int. Cl.[7] .............................................. C07C 45/45
(52) U.S. Cl. ........................ 568/319; 568/313; 568/319; 568/328; 568/331; 568/392; 568/406
(58) Field of Search .................... 568/312, 313, 568/315, 321, 328, 331, 332, 392, 406, 319

(56) References Cited

U.S. PATENT DOCUMENTS

| | | | | |
|---|---|---|---|---|
| 4,162,268 A | * | 7/1979 | Miyake et al. | |
| 5,126,489 A | * | 6/1992 | Kurek | |
| 5,434,310 A | * | 7/1995 | Waldmann et al. | |
| 5,476,970 A | * | 12/1995 | Rains et al. | |
| 6,184,418 B1 | * | 2/2001 | Dubac et al. | |

* cited by examiner

*Primary Examiner*—Sreeni Padmanabhan
*Assistant Examiner*—Sikarl A. Witherspoon
(74) *Attorney, Agent, or Firm*—Ladas & Parry

(57) ABSTRACT

The present invention provides a liquid phase process for the acylation of aromatic compound by an acylating agent of the formula $(R_5R_6R_7)$—Y—Z to obtain the corresponding acylated compound using a solid catalyst comprising a metal oxide of the formula $AO_x$ with or without a catalyst support, wherein A is a metallic element selected from Ga, In, Ti, Fe and a mixture of two or more thereof, and x is the number of oxygen atoms required to fulfil the valance requirement of A, wherein the catalyst is pretreated with a dry gas comprising a hydrogen halide in the presence or absence of the aromatic compound to be acylated, contacting the hydrogen halide pretreated catalyst with a liquid reaction mixture comprising the aromatic compound and the acylating agent, cooling the reaction mixture, removing the catalyst from the reaction mixture and then separating the reaction products from the reaction mixture.

26 Claims, No Drawings

PROCESS FOR THE LIQUID PHASE ACYLATION OF AROMATIC COMPOUNDS

FIELD OF THE INVENTION

The present invention relates to a process for the liquid phase acylation of aromatic compounds by an acylating agent using a solid catalyst comprising metal oxide(s). The present invention particularly relates to a process for the acylation of aromatic compounds using a reusable solid catalyst comprising metal oxide(s).

BACKGROUND OF THE INVENTION

Friedel Crafts type acylation of aromatic compounds by various acylating agents, using homogeneous Lewis acid catalysts, such as $AlCl_0$, $BF_3$, $ZnCl_2$ and other metal chlorides and protonic acid catalysts such as $H_2SO_4$, $H_3PO_4$, HF, etc., are well known in the art [G. A. Olah, in Friedel Crafts and related reactions: vol III, Acylation and related reactions, Wiley-Interscience Publ., New York, 1964].

U.S. Pat. No. 5,476,970 granted to Rains et al. Discloses a homogeneous liquid phase process for the acylation of $R_1R_2R_6H_4$ by $R_3R_4R_6H_3COCl$, wherein $R_1$, $R_2$, $R_3$ and $R_4$ are chemical groups using $FeCl_3$ catalyst at high pressures. French Patents FR 2768728 (1999) and FR 2768729 (1999) of Baudry et al, disclose liquid phase homogeneous process for the benzoylation of anisole by benzoyl chloride using rare earth halides or uranyl halide.

Japanese patent JP 08277241, A2 (1996) of Kunikata discloses a liquid phase process for the acylation of phenol by phenyl acetyl chloride using a homogeneous $AlCl_0$ catalyst. A use of $AlCl_0$ as a homogeneous catalyst is also disclosed by Oono for the acylation of toluene with acetyl chloride at high pressures in Japanese patent JP 09059205, A2 (1997). Japanese patent JP 20000086570, A2 (2000) of Shoji et al discloses a homogeneous liquid phase process for the acylation of toluene by acetyl fluoride using $HF-BF_3$ as a catalyst.

The main disadvantages of the Friedel-Crafts type acylation processes based on the use of the above mentioned homogeneous acid catalysts are:
1. The separation and recovery of the dissolved acid catalysts from the liquid reaction mixture is difficult.
2. The disposal of the used acid catalysts creates environmental pollution.
3. The homogeneous acid catalysts also result in problems such as high toxicity, corrosion, spent acid disposal and also require use of more than the stoichiometric amounts.

Liquid phase processes for the acylation of aromatic compounds by acyl halides using solid catalysts is also well known in the art.

Japanese patent JP 01089894, A2 (1995) to Myata et al discloses a liquid phase process for the acylation of toluene with benzoyl chloride using ammonium chloride treated H-beta zeolite catalyst under reflux for 3 hours to get para acylated toluene with 28% yield. French patent FR 2745287, A1 (1997) of Barbier et al discloses a liquid phase acylation of anisole by benzoyl chloride under reflux using neodymium chloride deposited on montmorillonite K—10 clay.

Vincent et al (ref Tetrahedron Lett., 35, 1994, 2601) disclose that H-ZSM-5 zeolite can catalyze the acylation of phenol and anisole by benzoyl chloride at 120° C. for 5 hours but not the acylation with benzoyl chloride of benzene and naphthalene.

Acylation of aromatic compounds involves the electrophilic substitution of H from the aromatic nucleus of the aromatic compound. It is well known in the prior art that the electrophilic substitution is favoured by the presence of electron donating groups such as OH, alkyl, alkoxy, phenoxy, amine, alkyl amine, SH, etc., in the aromatic compound. Whereas the electophilic substitution is inhibited by the presence of electron withdrawing groups such as halo, nitro, cyano. Carboxy, aldehyde, etc., in the aromatic compound [G. A. Olah, in Friedel Crafts and related reactions Wiley-Interscience Publ., New York, 1963].

While some limitations of the homogeneous acid catalysed processes are overcome in the prior art heterogeneous solid catalysed processes described above, the acylating activity of the solid acid catalysts used in the prior art processes is low, particularly for acylating aromatic compounds not containing electron donating groups, such as benzene, naphthalene etc. Both the prior art homogeneous and heterogeneous acid catalysts are highly moisture sensitive, and hence demand moisture free or thoroughly dried reactants, solvents and catalyst for Friedel-Crafts type acylation processes. In the presence of moisture in the reaction mixture, both the above homogeneous and heterogeneous catalysts show poor activity in the Friedel-Crafts type acylation processes. Hence there is a need for finding more efficient, reusable and also moisture insensitive solid catalyst for the acylation of aromatic compounds, which overcomes the disadvantages of the prior art discussed above.

OBJECTS OF THE INVENTION

The main object of the present invention is to provide a liquid phase process for the acylation of aromatic compounds including those which do not contain electron donating groups, using a solid catalyst, which has high activity when the aromatic ring activating groups (electron donating groups like alkyl, alkoxy, hydroxy, phenoxy, etc.) are present in the aromatic ring to be acylated and also when the ring activating groups in the aromatic ring to be acylated are absent, such that reaction temperature is low and/or reaction time is short.

Another object of the invention is to provide a liquid phase process for acylation of aromatic compounds using a solid catalyst that is easily separable and reusable in the process.

It is another object of the present invention to provide a liquid phase process for the acylation of aromatic compounds that is insensitive the presence of moisture in the reaction mixture.

SUMMARY OF THE INVENTION

Accordingly the present invention provides a liquid phase process for the acylation of aromatic compound of the formula $(R_1R_2R_3R_4)$—M—H by an acylating agent of the formula $(R_5R_6R_7)$—Y—Z to obtain the corresponding acylated compound of the formula $(R_1R_2R_3R_4)$—M—Y—$(R_5R_6R_7)$, wherein M is an aromatic nucleus with $R_1R_2R_3$, and $R_4$ being the chemical groups attached thereto, Y is the nucleus of the acylating agent and is selected from the group consisting of C—CO, $C_nH_{2n-2}CO$, $C_6H_2CO$, $C_6H_2C_nH_{2n}$—CO and $C_6H_2C_{n-1}(X)$—CO with $R_5$, $R_6$ and $R_7$ being chemical groups attached thereto Y, Z is selected from the group consisting of Cl, Br, I and OH, X is a halogen, and n is an integer having a value equal to or greater than 1.0, using a solid catalyst comprising a metal oxide of the formula $AO_x$ with or without a catalyst support, wherein A is a metallic element selected from Ga, In, Tl, Fe and a mixture of two or more thereof, and x is the number of oxygen atoms required to fulfil the valance requirement of A, the said process comprising, i. pretreating the solid catalyst by contacting it with a dry gas comprising a hydrogen halide in the presence or absence of the aromatic compound to be acylated;

ii. contacting the hydrogen halide pretreated catalyst with a liquid reaction mixture comprising the aromatic compound and the acylating agent in a stirred batch reactor at following reaction conditions: weight ratio of catalyst to acylating agent in the range of about 0.01 to about 2.0, mole ratio of the aromatic compound to the acylating agent in the range of from about 0.1 to 100, weight ratio of non-aqueous solvent to the aromatic compound being in the range of about 0 to about 100, reaction temperature being in the range of about 10° C. to about 300° C., pressure in the range of about 0.5 atm to about 10 atm., gas hourly space velocity of inert gas bubbled through the reaction mixture being in the range of about $0h^{-1}$ to 5000 $h^{-1}$ and reaction period in the range of from about 0.02 hours to about 100 hours;

iii. cooling the reaction mixture to a temperature of about 30° C., removing the catalyst from the reaction mixture by filtration and then separating the reaction products from the reaction mixture.

In another embodiment of the invention, $R_1R_2R_3$, and $R_4$ are each selected from hydrogen, alkane, olefininc, phenyl, alkoxy, phenoxy, hydroxyl, aldehydic, halogen, ketonic, amine, amide, thio, and sulphonic acid groups; Z is selected from Cl, Br, or OH, each of $R_5R_6$, and $R_7$ is selected from the group consisting of hydrogen, alkane, olefinic, phenyl, halogen, nitro and cyano groups, A is selected from Ga, In and Tl or a mixture of two or more thereof, the hydrogen halide used in step ii is selected from HCl and HBr, the weight ratio of the catalyst to the acylating agent is in the range of about 0.03 to 0.09, the mole ratio of the aromatic compound to the acylating agent is in the range of 1.0 to 20, the weight ratio of the non-aqueous solvent to the aromatic compound is in the range of 0 to 20, the reaction temperature is in the range of 20° C. to 200° C., the reaction pressure is in the range of 1 atm to 5 atm, the reaction period is in the range of 0.05 hours to 20 hours, and the space velocity of inert gas is in the range of $50h^{-1}$ to $500h^{-1}$.

In another embodiment of the invention, M is selected from the group comprising a single aromatic ring containing 6 C atoms and 1 H atom, fused two aromatic rings containing 10 C atoms and 3 H atoms, and three fused aromatic rings containing 14 C atoms and 5 H atoms.

In one embodiment of the invention, the used catalyst is washed with a non-aqueous solvent or aromatic substrate; and recycled directly with or without drying, to step i above.

In another embodiment of the invention, $R_1R_2R_3$, and $R_4$ are each selected from the group consisting of H, $C_nH_{2n+1}$, $C_mH_{2m+1}$, $C_6H_5$, $C_nH_{2n}C_6H_5$, OH, $OC_nH_{2n+1}$, O $C_6H_5$, halogen, $NO_2$, $NH_2$, NH $C_nH_{2n+1}$, $N(C_nH_{2n+1})_2$, NHCO $C_nH_{2n+1}$, $NHCOC_6H_5$, CN, CHO, COOH, $COOC_nH_{2n+1}$, $COC_nH_{2n+1}$, $SO_3H$, $SO_3C_nH_{2n+1}$, SH, alkyl mercapto and aryl mercapto wherein n and m are integers greater than or equal to 1 and 2 respectively.

In another embodiment of the invention, each of $R_5$, $R_6$, and $R_7$ is selected from the group consisting of H, $CH_3$, $C_2H_5$, OH, $OCH_3$, $OC_2H_5$, $NO_2$, halogen and $NH_2$.

In another embodiment of the invention, the preferred reaction temperature is in the range of 20° C. to 200° C., the preferred reaction time period is in the range of 0.1 hours to 20 hours, the preferred gas hourly space velocity of the inert gas bubbling through the reaction mixture is in the range of $50^{h-1}$ to $500^{h-1}$, the weight ratio of the catalyst to the acylating agent is in the range of about 0.1 to 1, the mole ratio of the aromatic compound to the acylating agent is in the range of 0.5 to 20, the weight ratio of the non-aqueous solvent to the aromatic compound is in the range of 0 to 20, Z is preferably Cl or Br, M is Ga or In or a mixture thereof, the preferred hydrogen halide used in step i is HCl or HBr, $R_1$, $R_2$, $R_3$, and $R_4$ are each selected from the group consisting of H, alkane ($C_nH_{2n+1}$), olefinic ($C_mH_{2m+1}$), phenyl ($C_6H_5$), alkoxy ($OC_nH_{2n+1}$), phenoxy ($OC_6H_5$), hydroxyl (OH), aldehydic (CHO), ketonic, amine ($NH_2$), amide (CO $NH_2$), sulfonic acid ($SO_3H$), and thio (SH), wherein n and m are integers greater than or equal to 1 and 2 respectively, each of $R_5$, $R_6$, and $R_7$ is selected from the group consisting of H, alkane($C_nH_{n+1}$), olefinic ($C_mH_{2m+1}$), phenyl ($C_6H_5$), haloge (Cl, Br, I or F), nitro ($NO_2$), and cyano (CN).

In another embodiment of the invention, the catalyst is supported on a meso or macroporous catalyst carrier selected from alumina, silica, silica-alumina, inert metal oxides, zeolites, and zeolite like materials.

In a further embodiment of the invention, the catalyst support comprises a zeolite material selected from the group consisting of microporous zeolites (pore size ≦1.0 nm) such as zeolite X, zeolite Y, mordenite, Zeolite L, zeolite beta, ZSM 5, ZSM 8, ZSM 11, and mesoporous zeolites (pore size=1.5 nm to 50 nm) such as M41S type material, MCM 41.

In another embodiment of the invention, the solvent when used is selected from the group consisting of dichloroethane, nitrobenzene, nitromethane, chlorobenzene, n-hexane, n-heptane and n-octane.

DETAILED DESCRIPTION OF THE INVENTION

It is observed that the catalyst used in the invention has a high activity in the acylation of aromatic compounds not only when electron donating groups, which is the aromatic ring activating group, is present in the aromatic ring to be acylated, but also when it is absent. Without being bound by the proposition, it is believed that this leads to lowering of the reaction temperature and reaction time requirements.

Another advantage observed is that the solid catalyst used can be separated and reused repeatedly in the process. It is also observed that the reaction rates are high even in the presence of moisture in the reaction mixture. Pretreatment of the solid catalyst with a hydrogen halide is essential in order to activate the catalyst.

The catalyst is supported on a meso or macroporous catalyst carrier selected from alumina, silica, silica-alumina, inert metal oxides, zeolites, and zeolite like materials. The zeolite material is selected from the group consisting of microporous zeolites (pore size ≦1.0 nm) such as zeolite X, zeolite Y, mordenite, Zeolite L, zeolite beta, ZSM 5, ZSM 8, ZSM 11, and mesoporous zeolites (pore size=1.5 nm to 50 nm) such as M41S type material, MCM 41. (Breck, Zeolite Molecular Sieves, Wiley Interscience Publ., New York, 1974; Beck et al, J. Am. Chem. Soc., vol. 114, page 10834, 1992; Nature (London) vol. 359, 710, 1992).

In general, micropores have diameter below 1 nm, mesopores have diameter between 1 nm and 20 nm and macropores have diameter above 20 nm. The catalyst supported on a microporous catalyst carrier is used generally when the both reactants have minimum molecular diameter or critical size of less than 0.7 nm. The mesoporous or macroporous catalyst carriers can be used irrespective of the size of the reactants. The reaction is carried out in a stirred batch reactor fitted with a reflex condenser and an arrangement for bubbling inert gas through the reaction mixture. Such arrangements are known in the art for liquid phase reactions.

In the reaction, the main product formed is the acylated aromatic compound of the formula $(R_1R_2R_3R_4)$—M—Y—$(R_5R_6R_7)$ while HZ is formed as a byproduct wherein $R_1$, $R_2$, $R_3$, $R_4$, M, Y, $R_5$, $R_6$, and $R_7$ and Z are as described above.

The process of the invention can be carried out with or without a non-aqueous solvent selected from dichloroethane, nitrobenzene, nitromethane, chlorobenzene, n-hexane, n-heptane and n-octane. The role of the solvent is to dissolve the solid reactant or reactants and thereby facilitate the reaction there between. The solvent is not necessary when both the reactants are liquid at reaction conditions. It is observed that the solvent when used is not converted during the process.

The inert gas is bubbled continuously through the reaction mixture in order to remove the byproduct form reaction mixture and thereby prevent or minimise reverse reaction. This helps to shorten the time of the reaction. The reaction takes place even in the absence of the inert gas but requires a longer time period and leads to incomplete conversion.

The reflux condenser fitted with the reactor is to condense the reactants and/or the solvent and to return them to the reaction mixture and allow the inert gas that is continuously bubbling through the reaction mixture to escape along with the reaction byproduct. The reaction pressure is normally above atmospheric pressure thereby allowing the reaction to proceed at a temperature higher than the normal boiling point of the reactants and/or solvent with increase in reaction pressure.

The catalyst used is heterogeneous with respect to the reaction mixture and can be removed from the reaction mixture by simple filtration and after washing with solvent or liquid aromatic compound which is to be acylated, recycled to the reaction mixture. The catalyst activates both the reactants and thereby increases the rate of the acylation reaction. During the pretreatment of the catalyst, the catalyst surface is changed by partial halidation causing modification of the active sites and/or creation of new active sites on the surface thereof. The pretreatment of the catalyst is critical to activate the catalyst. The pretreatment of the catalyst can be effected by:

1. contacting the solid catalyst with hydrogen halide gas in a closed vessel at room temperature for an effective period to activate the catalyst;
2. by passing a mixture of hydrogen halide and nitrogen or any other inert gas over the solid catalyst in a glass reactor at or above room temperature for a period of above 0.05 hours;
3. by passing a hydrogen halide gas with or without an inert gas such as nitrogen, argon, helium or the like through the reaction mixture containing the aromatic substrate, with or without the solvent, and the catalyst, in a stirred reactor at a temperature above about room temperature for a period above about 0.05 hours and then flashing the reaction mixture with an inert gas to remove physically adsorbed or absorbed hydrogen halide in the reaction mixture.

The present invention is described with respect to the following examples which are illustrative and are not to be taken as limiting the scope of the invention.

Definition of Terms Used in the Examples

Conversion of reactant (%)=mole % of the reactant converted in the process. All the ratios of the aromatic compound to the acylating agent are in terms of mole ratios. All the solid catalyst to acylating agent and solvent to aromatic compound ratios are in terms of weight ratios.

The flow rates of the inert gas is measured at 0° C. and 1 atm pressure. Gas hourly space velocity (GHSV) is the volume of gas measured at 0° C. and 1 atm pressure passed through unit volume of liquid reaction mixture per hour.

Ac and Aa represent the aromatic compound to be acylated and the acylating agent respectively.

EXAMPLE 1

This example illustrates the process of this invention for the liquid phase acylation of benzene by benzoyl chloride to benzophenone using $Ga_2O_3$ catalyst. The liquid phase acylation reaction over the solid catalyst was carried out in three steps:

i. The catalyst was pretreated by contacting it with hydrogen chloride gas in a closed vessel at room temperature for a period of 12 hours.

ii. The pretreated catalyst was then contacted with a 15 cm³ liquid reaction mixture containing aromatic compound to be acylated and an acylating agent with or without non-aqueous solvent, in a stirred batch reactor (capacity=25 cm³) and fitted with a reflex condenser, mercury thermometer dipped in the reaction mixture, and an inlet tube for passing gas through the reaction mixture, under vigorous stirring, while bubbling moisture free inert gas through the reaction mixture at the reaction conditions given in Table 1. The gaseous hydrogen halide if evolved during the reaction was measured quantitatively by absorbing it in aqueous NaOH solution by a simple acid-base titration suing phenolphthalein indicator.

iii. After the reaction, the reaction mixture was cooled to room temperature (30° C.) and the products and the unconverted reactants present in the reaction mixture, after separating the solid catalyst from it by filtration, were analyzed by a gas chromatograph with a thermal conductivity detector, using a SE 30 column and hydrogen as a carrier gas.

The solid catalyst used ($Ga_2O_3$) was prepared by calcining 25 g gallium nitrate in an air oven at 550° C. for 4 hours.

The results are included in Table 1.

EXAMPLE 2

This example illustrates the process for the liquid phase acylation of toluene by benzoyl chloride to methyl benzophenone, using $Ga_2O_3$ (20 wt %)/Si-MCM-41 catalyst. The liquid phase acylation reaction is carried out in three steps as in Example 1, at the reaction conditions given in Table 1.

The solid catalyst $Ga_2O_3$ (20 wt %)/Si-MCM-41 is prepared by impregnating 27.29 g gallium nitrate dissolved in 100 ml distilled water, on 50 g fine powder of Si-MCM-41 (prepared according to Choudhary et al. Indian Academy of Sciences, Chemical Sciences) Vol. 109, p 229, 1997) by incipient wetness technique, drying the impregnated mass in an air oven at 110° C. for 8 hours and calcining in air at 550° C. for 4 hours.

The results are included in Table 1.

EXAMPLE 3 and 4

These examples illustrate the preparation of benzene and toluene by benzoyl halide to the corresponding acylated compounds using $In_2O_3$ and $Ga_{0.67}In_{2.33}O_3$ (27 wt %)/Si-MCM-41 catalysts.

The liquid phase acylation over the solid catalyst was carried out in the three steps by the same procedure as in Example 1, except that in step i. the catalyst was pretreated by passing a mixture of hydrogen bromide and nitrogen (20 mol % HBr in $N_2$) over the catalyst in a glass reactor at 50° C. for a period of 0.7 hours. The reaction conditions are given in Table 1.

The catalysts used in these examples are prepared as follows:

$In_2O_3$ was prepared by calcining 25 g indium nitrate in an air oven at 600° C. for 4 hours.

The $Ga_{0.67}In_{2.33}O_3$ (27 wt %)/Si-MCM-41 was prepared by impregnating 4.09 gallium nitrate and 14.9 g indium nitrate dissolved in 50 ml distilled water on 25 g fine powder of Si-MCM-41 by incipient wetness technique, drying the impregnated mass in an air oven at 110° C. for 8 hours and calcining in air at 550° C. for 4.5 hours.

The results are included in Table 1.

EXAMPLES 5–16

These examples illustrate the process of the invention for the liquid phase acylation of aromatic compounds by different acylating agents to corresponding acylated aromatic compounds using different solid catalysts.

The liquid phase acylation reaction over the solid catalyst was carried out in three steps by the same procedure as in Example 1, except that in step i., the catalyst was pretreated by passing a mixture of hydrogen chloride and nitrogen (12mol % HCl in $N_2$) through the reaction mixture containing 13 ml benzene and the catalyst in a stirred reactor at 80° C. under reflux for a period of 0.5 hours, and washing the pretreated catalyst with the aromatic compound to be acylated (benzene or toluene) or the solvent to be used in the acylation reaction. The catalysts used in these examples are prepared as follows:

The $Ga_2O_3$ and $Ga_2O_3$ (20 wt %)/Si-MCM-41 catalysts were prepared by the procedure in Examples 1 and 2.

The $Ga_{1.0}In_{2.0}O_3$ catalyst was prepared by calcining a homogeneous mixture of 13.65 g gallium nitrate and 28.4 g indium nitrate in an air oven at 600° C. for 4 hours.

$Tl_2O$ (20 wt %)/SZ5564 was prepared by impregnating 5.01 g thallous nitrate dissolved in 14 ml distilled water on 20 g fine particles (>100 mesh) of SZ-5564 catalyst support (obtained from Norton Co. USA, main chemical composition being 94.1% ($ZrO_2+HfO_2$), 3.5% CaO, 1.6% $SiO_2$ and 0.41% $Al_2O_3$; surface area=0.1 $m^2g^{-1}$; porosity=45%) by incipient wetness technique, drying the impregnated mass in an air oven at 120° C. for 8 hours and calcining in air at 550° C. for 4 hours.

The $In_2O_3$ (20 wt %)/Si-MCM-41 was prepared by impregnating 28.41 g indium nitrate dissolved in 100 ml distilled water on 50 g fine powders of Si-MCM-41 by incipient wetness technique, drying the impregnated mass in an air oven at 110° C. for 8 hours and calcining in air at 600° C. for 4 hours.

The $Ga_{1.13}In_{1.87}O_3$ (8 wt %)/SA-5205 was prepared by impregnating a mixture of 4.09 gallium nitrate and 6.28 g indium nitrate dissolved in 35 ml distilled water on 50 g SA 5205 catalyst support (obtained from Norton Co., USA having main chemical composition: 11.8% $SiO_2$ and 86.1% $Al_2O_3$; surface area<0.01 $m^2g^{-1}$; pore volume=0.35 $cm^3g^{-1}$; and average pore diameter~200 μm and particle size= 100–150 mesh) by incipient wetness technique, drying the impregnated mass in an air oven at 100° C. for 15 hours and calcining in air at 600° C. for 2 hours.

The $In_2O_3$ (20 wt %)/H-beta was prepared by impregnating 28.41 g indium nitrate dissolved in 45 ml distilled water, on 25 g H-beta (prepared by the procedure described in Singh et al, Catalysis Letters, vol 32, p 327, 1995) by incipient wetness technique, drying the impregnated mass in an oven at 100° C. for 15 hours and calcining in air at 600° C. for 2 hours.

The $Ga_{2.0}In_{1.0}O_3$ (15 wt %)/H-beta was prepared by impregnating a mixture of 0.55 g gallium nitrate and 0.29 g indium nitrate dissolved in 18 ml distilled water on 10 g H-beta by incipient wetness technique drying the impregnated mass in an air oven at 100° C. for 15 hours and calcining in air at 600° C. for 2 hours.

The $Fe_{1.0}Ga_{2.0}O_3$ (15 wt %)/Si-MCM-41 was prepared by impregnating a mixture of 6.33 g ferric nitrate and 6.82 g gallium nitrate dissolved in 50 ml distilled water on 25 g fine powder of Si-MCM-41 by incipient wetness technique, drying the impregnated mass in an air oven at 110° C. for 8 hours and calcining in air at 450° C. for 4 hours.

$Fe_{0.6}Ga_{1.2}In_{1.2}O_3$ (25 wt %)/Si-MCM-41 was prepared by impregnating a mixture of 6.3 g ferric nitrate, 5.46 g gallium nitrate and 8.52 g indium nitrate dissolved in 50 ml distilled water on 25 g fine powder of Si-MCM-41 by incipient wetness technique, drying the impregnated mass in an air oven at 110° C. for 8 hours and calcining in air at 600° C. for 4 hours.

The results are in Table 2.

EXAMPLES 17–20

These comparative examples illustrate the process of this invention for the liquid phase acylation of aromatic compounds by different acylating agents to corresponding acylated aromatic compounds using solid catalysts as prepared in Examples 4 and 10, even when an appreciable level of moisture is present in the reactor.

The liquid phase acylation reaction over the solid catalyst is carried out in three steps by the procedure as described in Example 1, except that in step i. the catalyst was pretreated by passing a mixture of hydrogen chloride and nitrogen (12 mol % HCl in $N_2$) through the reaction mixture containing 13 ml benzene and the catalyst in a stirred reactor at 80° C. under reflux for a period of 0.5 hours, and washing the pretreated catalyst with the aromatic compound to be acylated (benzene or toluene). In the present case the reaction was carried out using moist benzene or toluene (benzene or toluene saturated with water at 30° C.). The reaction conditions and the results are given in Table 3. The results given Table 3 show that the catalyst of the invention catalyses the acylation reaction even when moisture is present in the reaction mixture.

EXAMPLES 21–24

These examples show the reusability of the catalyst used in the earlier examples for the acylation of aromatic compounds by the process of the invention.

The process of the invention for the liquid phase acylation of aromatic compounds which was already used in the earlier examples was carried out using the reactor and the same procedure as described in Example 1, except that step i. was avoided and before use the used catalyst was washed with the aromatic substrate or the solvent used in the acylation reaction.

The results showing the reusability of the catalyst of this invention in the process of the invention are given in Table 4.

EXAMPLES 25 and 26

These comparative examples illustrate the importance of the pretreatment of $In_2O_3$ catalyst prepared in Example 3 by hydrogen chloride in step i. of the provess of the invention for the acylation of benzene by benzoyl chloride.

The liquid phase acylation reaction over the catalyst was carried out by the procedure described in Example 1, except that the catalysts was not pretreated in step i. The results are included under Example 25 in Table 5. Whereas the results in Example 26 of Table 5 are for the catalyst pretreated in step i. according to the procedure described in Examples 5–16 and carrying out the reaction by the following procedures for step ii and step iii of Example 1.

A comparison of conversion of the acylating agent in Examples 25 and 26 show that HCl pretreated catalyst has a higher activity than catalyst without pretreatment.

EXAMPLES 27 and 28

These comparative examples illustrate the importance of pretreatment of the $Ga_2O_3$ (20 wt %)Si-MCM-41 catalyst prepared in Example 2 by hydrogen chloride in step i. of the process of the invention for the acylation of toluene by benzoyl chloride.

The liquid phase acylation reaction over the catalyst was carried out by the procedure described in Example 2, except that the catalysts was not pretreated in step i. The results are included under Example 27 in Table 5. Whereas the results in Example 28 of Table 5 are for the catalyst pretreated in step i. according to the procedure described in Examples 5–16 and carrying out the reaction by the following procedures for step ii and step iii of Example 2.

A comparison of conversion of the acylating agent in Examples 27 and 28 show that HCl pretreated catalyst has a higher activity than catalyst without pretreatment The observations and conclusions from Examples 1–28 are given below:
1. The pretreatment of the catalyst in the process of the invention is critical and essential to activate the catalyst of the invention and thereby obtain high catalytic activity, i.e. high conversion of reactants in acylation reactions.
2. The catalyst of the invention shows high activity for the acylation of different aromatic compounds even when there are no electron donating groups present in the aromatic compound.
3. The catalyst of the invention shows very high activity for the acylation of aromatic compounds even in the presence of moisture in the reaction mixture.
4. The catalyst used in the process of the invention can be reused in the process.

TABLE 1

Results of acylation of different aromatic compounds

| Example No. | Example 1 | Example 2 | Example 3 | Example 4 |
|---|---|---|---|---|
| Catalyst | $Ga_2O_3$ | $Ga_2O_3$ (20 wt %)/Si-MCM-41 | $In_2O_3$ | $Ga_2O_3In_2O_3$ (27 wt %)/Si-MCM-41 |
| Reactants: | | | | |
| Aromatic compound (Ac) | Benzene | Toluene | Benzene | Toluene |
| Acylating agent (Aa) | Benzoyl chloride | Benzoyl chloride | Benzoyl chloride | Benzoyl bromide |
| Reaction Conditions: | | | | |
| Solvent | Nil | Nil | Nil | Nil |
| Ac/Aa mole ratio | 17.0 | 15 | 17.0 | 17.0 |
| Solvent/Aa mole ratio | 0.0 | 0.0 | 0.0 | 0.0 |
| Catalyst/Ad weight ratio | 0.33 | 0.6 | 0.33 | 0.33 |
| Temperature (° C.) | 80 | 1 | 80 | 112 |
| Pressure (atm) | 1.0 | 1.8 | 1.0 | 1.1 |
| GHSV of $N_2$ ($h^{-1}$) | 99 | 99 | 99 | 55 |
| Reaction time (hours) | 3.5 | 1.0 | 2.5 | 2.6 |
| Conversion of Aa (%) | 37.2 | 85 | 42.6 | 81.2 |
| Main product of reaction | $C_6H_5COC_6H_5$ | $CH_3C_6H_4COC_6H_5$ | $C_6H_5COC_6H_5$ | $CH_3C_6H_4COC_6H_5$ |
| Byproduct of reaction | HCl | HCl | HCl | HBr |
| Example No. | Example 5 | Example 6 | Example 7 | Example 8 |
| Catalyst | $Ga_2O_3$ | $Ga_{1.0}In_{2.0}O_3$ | $Tl_2O$ (20 wt %)/ SZ5564 | $Ga_2O_3O_3$ (27 wt %)/Si-MCM-41 |
| Reactants: | | | | |
| Aromatic compound (Ac) | Benzene | p-Xylene | Toluene | Durene |
| Acylating agent (Aa) | Benzoyl chloride | Benzoyl bromide | Benzoyl chloride | Benzoyl chloride |
| Reaction Conditions: | | | | |
| Solvent | Nil | Nil | Nil | Dichloroethane |
| Ac/Aa mole ratio | 17.0 | 15 | 17.0 | 2.5 |
| Solvent/Aa mole ratio | 0.0 | 0.0 | 0.0 | 20.0 |
| Catalyst/Aa weight ratio | 0.33 | 0.30 | 0.33 | 0.5 |
| Temperature (° C.) | 80 | 140 | 110 | 80 |
| Pressure (atm) | 1.0 | 1.0 | 1.0 | 1.0 |
| GHSV of $N_2$ ($h^{-1}$) | 99 | 99 | 99 | 99 |
| Reaction time (hours) | 3.6 | 1.0 | 2.0 | 2.5 |
| Conversion of Aa (%) | 54.7 | 97 | 90.1 | 97.2 |
| Main product of reaction | $C_6H_5COC_6H_5$ | $(CH_3)_2C_6H_3COC_6H_5$ | $CH_3C_6H_4COC_6H_5$ | $(CH_3)_4C_6H_4COC_6H_5$ |
| Byproduct of reaction | HCl | HBr | HCl | HBr |

TABLE 2

Results of the acylation of different aromatic compounds

| Example No. | Example 9 | Example 10 | Example 11 | Example 12 |
|---|---|---|---|---|
| Catalyst | $Ga_2O_3$ (20 wt %)/Si-MCM-41 | $In_2O_3$ (20 wt %)/Si-MCM-41 | $In_2O_3$ (20 wt %)/Si-MCM-41 | $Ga_{1.13}In_{1.87}O_3$ (8 wt %)/SA-5205 |
| Reactants: | | | | |
| Aromatic compound (Ac) | 2-methoxy naphthalene | 2-Naphthol | Phenol | Phenol |
| Acylating agent (Aa) | Acetyl chloride | Acetyl chloride | Benzoyl chloride | Acetyl chloride |
| Reaction Conditions: | | | | |
| Solvent | Dichloroethane | Dichloroethane | Dichloroethane | Dichloroethane |
| Ac/Aa mole ratio | 2.3 | 2.1 | 2.5 | 1.5 |
| Solvent/Aa mole ratio | 21 | 20 | 23 | 16 |
| Catalyst/Aa weight ratio | 0.33 | 0.1 | 0.33 | 0.3 |
| Temperature (° C.) | 35 | 30 | 80 | 45 |
| Pressure (atm) | 1.0 | 1.0 | 1.0 | 1.3 |
| GHSV of $N_2$ ($h^{-1}$) | 85 | 90 | 110 | 115 |
| Reaction time (hours) | 6.6 | 1.5 | 0.25 | 0.8 |
| Conversion of Aa (%) | 98.7 | 96.2 | 99.3 | 98.3 |
| Main product of reaction | $(CH_3O)C_{10}H_6COCH_3$ | $(HO)C_{10}H_6COCH_3$ | $(HO)C_6H_4COC_6H_5$ | $(HO)C_6H_4COCH_3$ |
| Byproduct of reaction | HCl | HCl | HCl | HCl |

| Example No. | Example 13 | Example 14 | Example 15 | Example 16 |
|---|---|---|---|---|
| Catalyst | $In_2O_3$ (40 wt %)/H-beta | $Ga_{2.0}In_{1.0}O_3$ (3 wt %)/H-beta | $Fe_{1.0}Ga_{2.0}O_3$ (15 wt %)/Si-MCM-41 | $Fe_{0.6}Ga_{1.2}In_{1.2}O_3$ (25 wt %)/Si-MCM-41 |
| Reactants: | | | | |
| Aromatic compound (Ac) | Phenol | Phenol | Mesitylene | Naphthalene |
| Acylating agent (Aa) | Acetic acid | Phenyl acetyl chloride | Benzoyl bromide | Butyryl chloride |
| Reaction Conditions: | | | | |
| Solvent | Nil | Dichloroethane | Nil | Dichloroethane |
| Ac/Aa mole ratio | 0.5 | 2.1 | 7.0 | 0.5 |
| Solvent/Aa mole ratio | 0.0 | 18.0 | 0.0 | 15 |
| Catalyst/Ad weight ratio | 0.5 | 0.9 | 0.8 | 1.0 |
| Temperature (° C.) | 140 | 85 | 175 | 80 |
| Pressure (atm) | 1.0 | 1.2 | 1.4 | 1.3 |
| GHSV of $N_2$ ($h^{-1}$) | 125 | 93 | 120 | 0.0 |
| Reaction time (hours) | 12.5 | 1.1 | 0.25 | 4.7 |
| Conversion of Aa (%) | 22.3 | 99.1 | 92.0 | 98.5 |
| Main product of reaction | $(HO)C_6H_4COCH_3$ | $(HO)C_6H_4COCH_2C_6H_5$ | $(CH_3)_3C_6H_2COC_6H_5$ | $C_{10}H_7COC_4H_9$ |
| Byproduct of reaction | $H_2O$ | HCl | HBr | HCl |

TABLE 3

Results of the acylation of different aromatic compounds

| Example No. | Example 17 | Example 18 | Example 19 | Example 20 |
|---|---|---|---|---|
| Catalyst | $In_2O_3$ (20 wt %)/Si-MCM-41 | Same as in Example 17 | $Ga_{0.67}In_{2.33}O_3$ (27 wt %)/Si-MCM-41 | Same as in Example 19 |
| Reactants: | | | | |
| Aromatic compound (Ac) | Benzene | Benzene saturated with water | Toluene | Toluene saturated with water |
| Acylating agent (Aa) | Benzoyl chloride | Benzoyl chloride | Benzoyl bromide | Benzoyl bromide |
| Reaction Conditions: | | | | |
| Solvent | Nil | Nil | Nil | Nil |
| Ac/Aa mole ratio | 15.7 | 15.7 | 17.0 | 17.0 |
| Solvent/Aa mole ratio | 0.0 | 0.0 | 0.0 | 0.0 |
| Catalyst/Aa weight ratio | 0.52 | 0.52 | 0.33 | 0.33 |
| Temperature (° C.) | 80 | 80 | 112 | 112 |
| Pressure (atm) | 1.0 | 1.0 | 1.1 | 1.1 |
| GHSV of $N_2$ ($h^{-1}$) | 95 | 95 | 55 | 55 |
| Reaction time (hours) | 2.5 | 2.4 | 2.6 | 2.3 |
| Conversion of Aa (%) | 52.1 | 52.3 | 93.4 | 95.2 |

TABLE 3-continued

Results of the acylation of different aromatic compounds

| Example No. | Example 17 | Example 18 | Example 19 | Example 20 |
|---|---|---|---|---|
| Main product of reaction | $C_6H_5COC_6H_5$ | $C_6H_5COC_6H_5$ | $(CH_3)C_6H_4COC_6H_5$ | $(CH_3)C_6H_4COC_6H_5$ |
| Byproduct of reaction | HCl | HCl | HBr | HBr |

TABLE 4

Results showing the reusability of the catalyst of the invention for the process of the invention

| Example No. | Example 21 | Example 22 | Example 23 | Example 24 |
|---|---|---|---|---|
| Catalyst | The catalyst after its use in Example 19 | The catalyst after its use in Example 21 | The catalyst after its use in Example 16 | The catalyst after its use in in Example 19 |
| Reactants: | | | | |
| Aromatic compound (Ac) | p-xylene | Anisole | Benzene | Naphthalene |
| Acylating agent (Aa) | Benzoyl chloride | Butyryl chloride | Benzoyl chloride | Propionyl chloride |
| Reaction Conditions: | | | | |
| Solvent | Nil | Nil | Nil | Nitromethane |
| Ac/Aa mole ratio | 17.9 | 16.5 | 17.1 | 2.0 |
| Solvent/Aa mole ratio | 0.0 | 0.0 | 0.0 | 15.0 |
| Catalyst/Aa weight ratio | 0.3 | 0.25 | 0.8 | 0.5 |
| Temperature (° C.) | 140 | 163 | 87 | 103 |
| Pressure (atm) | 1.0 | 1.3 | 1.5 | 1.2 |
| GHSV of $N_2$ ($h^{-1}$) | 105 | 95 | 97 | 91 |
| Reaction time (hours) | 1.0 | 1.5 | 9.0 | 2.8 |
| Conversion of Aa (%) | 97.9 | 97.5 | 98.4 | 98.6 |
| Main product of reaction | $(CH_3)_2C_6H_3COC_6H_5$ | $(CH_3O)C_6H_4COC_4H_9$ | $C_6H_5COC_6H_5$ | $C_{10}H_7COC_3H_7$ |
| Byproduct of reaction | HCl | HCl | HCl | HCl |

TABLE 5

Results of acylation of different aromatic compounds with and without pretreatment of catalyst.

| Example No. | Example 25 | Example 26 | Example 27 | Example 28 |
|---|---|---|---|---|
| Catalyst | $In_2O_3$ | $In_2O_3$ | $Ga_2O_3$ (20 wt %)/Si-MCM-41 | $Ga_2O_3$ (20 wt %)/Si-MCM-41 |
| Reactants: | | | | |
| Aromatic compound (Ac) | Benzene | Benzene | Toluene | Toluene |
| Acylating agent (Aa) | Benzoyl chloride | Benzoyl chloride | Benzoyl chloride | Benzoyl chloride |
| Reaction Conditions: | | | | |
| Solvent | Nil | Nil | Nil | Nil |
| Ac/Aa mole ratio | 17.0 | 17.0 | 15 | 15 |
| Solvent/Aa mole ratio | 0.0 | 0.0 | 0.0 | 0.0 |
| Catalyst/Aa weight ratio | 6.33 | 0.33 | 0.6 | 0.6 |
| Temperature (° C.) | 80 | 80 | 117 | 117 |
| Pressure (atm) | 1.0 | 1.0 | 1.8 | 1.8 |
| GHSV of $N_2$ ($h^{-1}$) | 99 | 99 | 99 | 99 |
| Reaction time (hours) | 2.6 | 2.8 | 1.0 | 1.0 |
| Conversion of Aa (%) | 31.3 | 52.5 | 77 | 95.1 |
| Main product of reaction | $C_6H_5COC_6H_5$ | $C_6H_5COC_6H_5$ | $CH_3C_6H_4COC_6H_5$ | $CH_3C_6H_4COC_6H_5$ |
| Byproduct of reaction | HCl | HCl | HCl | HCl |

ADVANTAGES OF THE INVENTION

The process of the invention has the following advantages over the prior art homogeneous acid catalysed processes for the acylation of aromatic compounds.

1. The catalyst used is a heterogeneous solid catalyst and hence can be separated from the reaction products simply by filtration.
2. The separated catalysts can be reused a number of times in the process of the invention.
3. The catalyst is non-corrosive.

The process of the invention can be differentiated from prior art processes bsed on the use of solid acid catalyst for the acylation of aromatic reactions.

1. The activity of the catalyst used in the invention is high thereby increasing the speed of reaction and reducing the time required for completion of the reaction.
2. The catalyst of the invention can be reused a number of times in the process of the invention and shows high activity in the process even after repeated use.
3. The process of the invention can be used for the acylation of both small and large size aromatic compounds with both small and large sized acylating agents to obtain the corresponding acylated aromatic compounds.

4. When the inert gas is bubbled through the reaction mixture continuously, the byproduct formed is removed continuously thereby preventing or minimising the reverse acylation reaction. This results in speeding up of the time required for the reaction.

5. By using pressures of greater than or equal to 1 atm., the reaction can be carried out at temperatures higher than the normal boiling point of either the reactants or the solvent, thereby shortening the reaction period. The inhibition of the reaction is avoided or minimised due to strong adsorption of the reactants, products or solvent on the catalyst.

6. The process of the invention is effective even for the acylation of benzene which does not contain any aromatic ring activating electron donating group such as alkyl, alkoxy, hydroxy, etc. The rate of reaction is rapid at mild reaction conditions and hence the time for reaction is short.

7. The process of the invention results in rapid acylation of aromatic compounds even when the reaction mixture contains moisture. The catalyst is not deactivated due to the presence of moisture in the reaction mixture. Thus, unlike prior art homogeneous and solid acid catalysts, the catalyst of the invention does not require moisture free conditions to be active. This results in saving of costs towards removal of moisture from the reaction system or the reactants.

8. The catalyst of the invention is acidic and basic in nature, the process of the invention can be used for acylating both acid sensitive aromatic compounds and basic aromatic compounds.

We claim:

1. A liquid phase process for the acylation of aromatic compound of the formula $(R_1R_2R_3R_4)$—M—H by an acylating agent of the formula $(R_5R_6R_7)$—Y—Z to obtain the corresponding acylated compound of the formula $(R_1R_2R_3R_4)$—M—Y—$(R_5R_6R_7)$, wherein M is an aromatic nucleus with $R_1R_2R_3$, and $R_4$ being the chemical groups attached thereto, Y is the nucleus of the acylating agent and is selected from the group consisting of C—CO, $C_nH_{2n-2}CO$, $C_6H_2CO$, $C_6H_2C_nH_{2n}$—CO and $C_6H_2C_nH_{2n-1}(X)$—CO with $R_5$, $R_6$ and $R_7$ being chemical groups attached thereto Y, Z is selected from the group consisting of Cl, Br, I and OH, X is a halogen, and n is an integer having a value equal to or greater than 1.0, using a solid catalyst comprising a metal oxide of the formula $AO_x$ with or without a catalyst support, wherein A is a metallic element selected from Ga, In, Tl, Fe and a mixture of two or more thereof, and x is the number of oxygen atoms required to fulfil the valance requirement of A, the said process comprising, i. pretreating the solid catalyst by contacting it with a dry gas comprising a hydrogen halide in the presence or absence of the aromatic compound to be acylated;

ii. contacting the hydrogen halide pretreated catalyst with a liquid reaction mixture comprising the aromatic compound and the acylating agent in a stirred batch reactor at following reaction conditions: weight ratio of catalyst to acylating agent in the range of about 0.01 to about 2.0, mole ratio of the aromatic compound to the acylating agent in the range of from about 0.1 to 100, weight ratio of non-aqueous solvent to the aromatic compound being in the range of about 0 to about 100, reaction temperature being in the range of about 10° C. to about 300° C., pressure in the range of about 0.5 atm to about 10 atm., gas hourly space velocity of inert gas bubbled through the reaction mixture being in the range of about 0 $h^{-1}$ to 5000 $h^{-1}$ and reaction period in the range of from about 0.02 hours to about 100 hours;

iii. cooling the reaction mixture to a temperature of about 30° C., removing the catalyst from the reaction mixture by filtration and then separating the reaction products from the reaction mixture.

2. A process as claimed in claim 1 wherein $R_1$, $R_2$, $R_3$, and $R_4$ are each selected from hydrogen, alkane, olefinic, phenyl, alkoxy, phenoxy, hydroxyl, aldehydic, halogen, ketonic, amine, amide, thio, and sulphonic acid groups.

3. A process as claimed in claim 1 wherein Z comprises Cl, Br, or OH.

4. A process as claimed in claim 1 wherein each of $R_5$, $R_6$, and $R_7$ is selected from the group consisting of hydrogen, alkane, olefinic, phenyl, halogen, nitro and cyano groups.

5. A process as claimed in claim 1 wherein A is selected from the group consisting of Ga, In and Tl and a mixture of any two or more thereof.

6. A process as claimed in claim 1 wherein the hydrogen halide used in step ii is selected from HCl gas and HBr gas.

7. A process as claimed in claim 1 wherein the weight ratio of the catalyst to the acylating agent is in the range of 0.03 to 0.09.

8. A process as claimed in claim 1 wherein the mole ratio of the aromatic compound to the acylating agent is in the range of 1.0 to 20.

9. A process as claimed in claim 1 wherein the weight ratio of the non-aqueous solvent to the aromatic compound is in the range of 0 to 20.

10. A process as claimed in claim 1 wherein the reaction temperature is in the range of 20° C. to 200° C.

11. A process as claimed in claim 1 wherein the reaction pressure is in the range of 1 atm to 5 atm.

12. A process as claimed in claim 1 wherein the reaction period is in the range of 0.05 hours to 20 hours.

13. A process as claimed in claim 1 wherein the space velocity of inert gas is in the range of 50 $h^{-1}$ to 500 $h^{-1}$.

14. A process as claimed in claim 1 wherein M is selected from the group comprising a single aromatic ring containing 6 C atoms and 1 H atom, fused two aromatic rings containing 10 C atoms and 3 H atoms, and three fused aromatic rings containing 14 C atoms and 5 H atoms.

15. A process as claimed in claim 1 wherein the used catalyst is washed with a non-aqueous solvent or the aromatic compound and recycled directly with or without drying to step ii.

16. A process as claimed in claim 1 wherein $R_1$, $R_2$, $R_3$, and $R_4$ are each selected from the group consisting of H, $C_nH_{2n+1}$, $C_mH_{2m+1}$, $C_6H_5$, $C_nH_{2n}C_6H_5$, OH, $OC_nH_{2n+1}$, O $C_6H_5$, halogen, $NO_2$, $NH_2$, NH $C_nH_{2n+1}$, $N(C_nH_{2n+1})_2$, NHCO $C_nH_{2n+1}$, $NHCOC_6H_5$, CN, CHO, COOH, $COOC_nH_{2n+1}$, $COC_nH_{2n+1}$, $SO_3H$, $SO_3C_nH_{2n+1}$, SH, alkyl mercapto and aryl mercapto wherein n and m are integers greater than or equal to 1 and 2 respectively.

17. A process as claimed in claim 1 wherein each of $R_5$, R6,and $R_7$ is selected from the group consisting of H, $CH_3$, $C_2H_5$, OH, $OCH_3$, $OC_2H_5$, $NO_2$, halogen and $NH_2$.

18. A process as claimed in claim 12 wherein the reaction time period is in the range of 0.1 hours to 20 hours.

19. A process as claimed in claim 7 wherein the weight ratio of the catalyst to the acylating agent is in the range of 0.1 to 1.

20. A process as claimed in claim 8 wherein the mole ratio of the aromatic compound to the acylating agent is in the range of 0.5 to 20.

21. A process as claimed in claim 3 wherein Z is Cl or Br.

22. A process as claimed in claim 14 wherein M is Ga or In or a mixture thereof.

23. A process as claimed in claim 1 wherein the catalyst is supported on a meso or macroporous catalyst carrier selected from alumina, silica, silica-alumina, inert metal oxides, zeolites, and zeolite like materials.

24. A process as claimed in claim 23 wherein the catalyst support comprises a microporous zeolite material (pore size $\leq 1.0$ nm) selected from the group consisting of selected from zeolite X, zeolite Y, mordenite, Zeolite L, zeolite beta, ZSM 5, ZSM 8 and ZSM 11.

25. A process as claimed in claim 23 wherein the catalyst support comprises a mesoporous zeolite material (pore size= 1.5 nm to 50 nm) selected from the group consisting of M41S type material and MCM 41.

26. A process as claimed in claim 1 wherein the solvent when used is selected from the group consisting of dichloroethane, nitrobenzene, nitromethane, chlorobenzene, n-hexane, n-heptane and n-octane.

* * * * *